(12) United States Patent
Evans

(10) Patent No.: US 11,344,419 B1
(45) Date of Patent: May 31, 2022

(54) TOTAL KNEE JOINT MOLD AND METHODS FOR GAP BALANCING AND JOINT LINE RESTORATION

(71) Applicant: Richard P. Evans, Broomfield, CO (US)

(72) Inventor: Richard P. Evans, Broomfield, CO (US)

(73) Assignee: Richard P. Evans, Broomfield, CO (US)

( * ) Notice: Subject to any disclaimer, the term of this patent is extended or adjusted under 35 U.S.C. 154(b) by 0 days.

(21) Appl. No.: 17/402,224

(22) Filed: Aug. 13, 2021

(51) Int. Cl.
 *A61F 2/38* (2006.01)
 *A61F 2/30* (2006.01)
 *A61B 17/88* (2006.01)
 *A61F 2/46* (2006.01)

(52) U.S. Cl.
 CPC ...... *A61F 2/30942* (2013.01); *A61B 17/8825* (2013.01); *A61F 2/389* (2013.01); *A61F 2/3859* (2013.01); *A61F 2/461* (2013.01); *A61F 2002/3069* (2013.01); *A61F 2002/30617* (2013.01); *A61F 2002/30677* (2013.01); *A61F 2002/30957* (2013.01); *A61F 2002/4658* (2013.01); *A61F 2310/00353* (2013.01)

(58) Field of Classification Search
 CPC ..... A61F 2/389; A61F 2/3859; A61B 17/8825
 See application file for complete search history.

(56) References Cited

U.S. PATENT DOCUMENTS

| | | | |
|---|---|---|---|
| 2,505,507 | A | 4/1950 | Sennholtz et al. |
| 2,642,009 | A | 6/1953 | Orfitelli |
| 3,028,283 | A | 4/1962 | Lundgren et al. |
| 3,161,917 | A | 12/1964 | Wiland |
| 3,237,910 | A | 3/1966 | Lavedas |
| 3,353,220 | A | 11/1967 | Lenoble |
| 3,964,106 | A | 6/1976 | Hutter, Jr. et al. |
| 4,209,861 | A | 7/1980 | Walker et al. |
| 4,247,075 | A | 1/1981 | Rogers |
| 4,898,359 | A | 2/1990 | Gopon |
| 4,938,906 | A | 7/1990 | Brault |
| 5,123,927 | A | 6/1992 | Duncan et al. |
| 5,171,282 | A | 12/1992 | Pequignot |

(Continued)

OTHER PUBLICATIONS

Kurtz SM et al., "International survey of primary and revision total knee replacement," *International Orthopaedics (SICOT)* Dec. 2011; 35(12):1783-1789, DOI 10.1007/s00264-011-1235-5.

(Continued)

*Primary Examiner* — Jason-Dennis N Stewart

(57) ABSTRACT

A femoral component kit includes a piston. The piston includes a notch formed in a bottom surface. The kit includes a femoral component mold having a mold body with a first sidewall, a second sidewall, and a bottom. The sidewalls and bottom define a recess for receiving an antibiotic-impregnated material. The recess includes depressed sections that are spaced apart by an inner section. The outer sections are transverse to a longitudinal axis of the mold. The inner section includes a keel that extends upward and has a height that sets a size of a femoral component produced using the mold. The keel is aligned with the notch when the piston is inserted within the mold. The notch and the keel may include one or more calibration markings that indicate increments of adjustments to the size of the femoral component and resulting flexion and extension gaps and joint space position.

20 Claims, 18 Drawing Sheets

(56) References Cited

U.S. PATENT DOCUMENTS

| | | |
|---|---|---|
| 5,226,915 A | 7/1993 | Bertin |
| 5,480,444 A | 1/1996 | Incavo et al. |
| 5,639,279 A | 6/1997 | Burkinshaw et al. |
| 5,980,573 A | 11/1999 | Shaffner |
| 5,996,963 A | 12/1999 | Michael |
| 6,013,103 A | 1/2000 | Kaufman et al. |
| 6,342,075 B1 | 1/2002 | MacArthur |
| 6,355,705 B1 | 3/2002 | Bond et al. |
| 6,506,215 B1 | 1/2003 | Letot et al. |
| 7,131,626 B2 | 11/2006 | Cole |
| 7,427,296 B2 | 9/2008 | Evans |
| 8,097,039 B2 | 1/2012 | Evans |
| 8,123,813 B2 | 2/2012 | Metzger et al. |
| 8,858,207 B2 | 10/2014 | Evans |
| 2005/0061947 A1 | 3/2005 | Smirnov et al. |
| 2005/0107885 A1 | 5/2005 | Evans |
| 2009/0295035 A1 | 12/2009 | Evans |
| 2012/0193509 A1 | 8/2012 | Evans |

OTHER PUBLICATIONS

Evans, Richard P MD et al. The Classic: The Effect of Wound Environment on the Incidence of Acute Osteomyelitis. vol. 439, Oct. 2005, 6 pages. Doi:10.1097/01.blo.0000183276.33237.24 https://journals.lww.com/clinorthop/toc/2005/10000.

U.S. Appl. No. 12/194,436, filed Aug. 19, 2008, Non-Final Rejection dated Jul. 29, 2010, all pages.

U.S. Appl. No. 12/194,436, filed Aug. 19, 2008, Final Rejection dated Feb. 7, 2011, all pages.

U.S. Appl. No. 13/350,253, filed Jan. 13, 2012, Non-Final Rejection dated Apr. 30, 2013, all pages.

U.S. Appl. No. 13/350,253, filed Jan. 13, 2012, Final Rejection dated Oct. 11, 2013, all pages.

U.S. Appl. No. 13/350,253, filed Jan. 13, 2012, Advisory Action dated Dec. 18, 2013, all pages.

U.S. Appl. No. 13/350,253, filed Jan. 13, 2012, Non-Final Rejection dated Apr. 10, 2014, all pages.

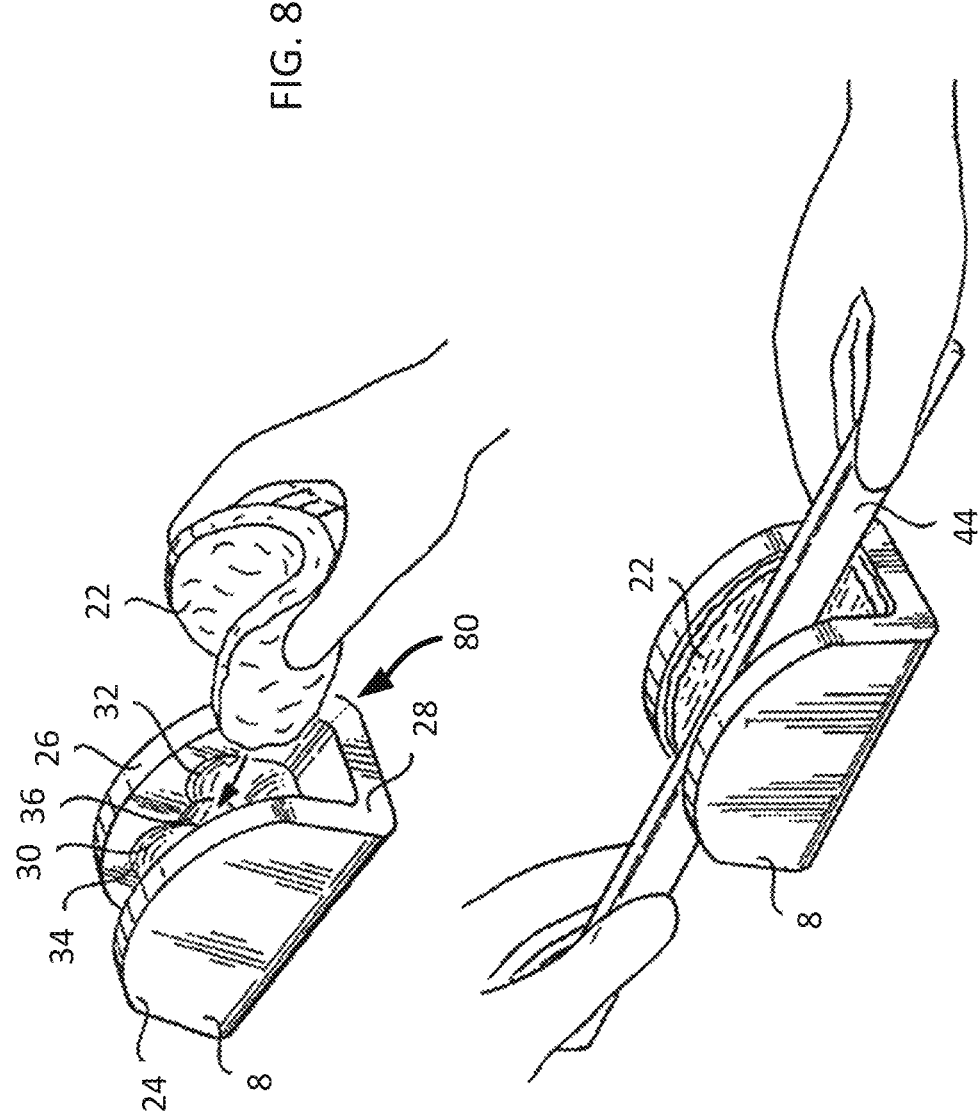

TOTAL KNEE JOINT MOLD AND METHODS FOR GAP BALANCING AND JOINT LINE RESTORATION

BACKGROUND OF THE INVENTION

Globally, total knee arthroplasty (TKA) is being performed at a rapidly increasing rate. In the United States, in 2020 up to 1,065,000 total knee arthroplasty procedures (also known as total knee replacements) were performed. In 2019, 2.6 million TKA were performed worldwide. Growth of 673% from 2007 projections to 3.48 million annual procedures by 2030 is projected in the US alone, [1]. Kurtz S M, Ong K L, Lau E, et al. International survey of primary and revision total knee replacement. Int Orthop. 2011 December; 35(12):1783-1789. A typical total knee replacement procedure involves resurfacing of the tibial plateaus and the femoral condyle. Holes are then drilled into the femur and the tibia. A metallic femoral component is then inserted into the femur and a metallic tibial component is inserted into the tibia. Bone cement usually holds the two components in place. These two components work together to replace the diseased knee joint and to simulate the function of a normal knee joint. One example of a total knee replacement surgery is described in U.S. Pat. No. 6,342,075, the complete disclosure of which is herein incorporated by reference.

About two to three percent of total knee replacements become deeply infected. When these components are simply replaced by new components the rate of cure of the infection is low compared to a two-stage surgical treatment where the components are removed and the infection treated before new components are re-implanted. Leaving or reintroducing metal into the joint as in a one stage reconstruction, will aggravate treatment of the infection. (THE CLASSIC: The Effect of Wound Environment on the Incidence of Acute Osteomyelitis. Evans, Richard P MD; Nelson, Carl L MD; Harrison, Barry H MS; Sherk, Henry H MD. https://journals.lww.com/clinorthop/toc/2005/10000.) Alternatively, standard two-stage surgical reconstruction includes removing the femoral and tibial components and replacing them with a puck-shaped spacer or void shaped spacer made of bone cement that is impregnated with an antibiotic or a fixed mass of antibiotic impregnated cement that fills the dead space left by the removal of the infected prosthetic components. This spacer is placed between the femur and the tibia for six to twelve weeks. The antibiotic in the spacer leaches out over time to treat the infection. When the infection is contained, the spacer is removed and the femoral and tibial components are once again inserted. Such a process is described in U.S. Pat. No. 5,980,573, the complete disclosure of which is herein incorporated by reference.

One problem with the use of such a spacer is that there is no knee joint while the infection is being treated. As such, the leg cannot move or bend. Often the spacer is loose and painful and the knee will scar down and will stiffen up, resulting in painful rehabilitation, loss of final normal range of motion and function, among other ailments. This may continue indefinitely and also makes the final replacement surgery itself technically more difficult because of the scarring and loss of motion and knee joint space at the time of re-implantation of new permanent components.

The closer to normal motion that can be achieved during treatment is directly proportional to the ease and result of the final reconstruction. Attempts at treatment of infected knee prosthesis with articulated temporary components have ignored well established principles of joint line and flexion and extension gaps restoration that are required for every single successful primary and revision knee replacement surgery. Consequently, when the joint line, and flexion and extension gaps required in every knee replacement surgery are not restored, full range of motion is not achieved, flexion and/or extension gap inequality result in contracture and/or instability that makes a positive outcome of the final second stage reconstruction proportionally difficult and sometimes impossible.

BRIEF SUMMARY OF THE INVENTION

Embodiments of the present technology may encompass a method for treating an infected area associated with a total knee replacement. The method may include providing a piston comprising a piston body, the piston body comprising a notch formed in a bottom surface of the piston body. The method may include providing a femoral component mold. The mold may include a mold body having a first sidewall, a second sidewall, and a bottom. The first sidewall, the second sidewall, and the bottom may each at least partially define a recess that extends continuously from the first sidewall through the bottom to the second sidewall. The recess may include two depressed outer arched sections that are spaced apart from each other by an inner section. The outer arched sections may be transverse to a longitudinal axis of the mold. The inner section may include a keel that extends upward from the bottom of the mold body. The keel may be aligned with the notch when the piston is inserted within the femoral component mold. One or both of the notch and the keel may include one or more calibration markings that indicate increments of adjustments to a size of a femoral component formed using the femoral component mold. The method may include setting the size of the femoral component based on a measured flexion-extension gap and a measured joint line position of a prior knee structure. The size of the femoral component may be determined by a height of the keel of the femoral component mold and a depth of the notch in the piston. The method may include positioning bone cement within the recess of the femoral component mold. The method may include compressing the bone cement within the femoral component mold using the piston to form the femoral component. The method may include removing the femoral component from the femoral component mold after the femoral component has at least partially set.

In some embodiments, the method may include mixing a bone cement powder with a monomer and a surgeon-determined amount and type of one or more antibiotics to form the bone cement. The method may include measuring the flexion-extension gap and the joint line position of the prior knee structure. The method may include applying the femoral component to a femur of a patient. The at least one marking may be provided on the keel. Setting the size of the femoral component may include reducing the height of the keel to match one of the at least one marking on the keel. The at least one marking may be provided on the piston. Setting the size of the femoral component may include increasing a depth of the notch of the piston to match one of the at least one marking on the piston. Removing the femoral component from the mold may include breaking the mold by disengaging the first sidewall from the bottom.

Embodiments of the present technology may encompass a mold for forming a femoral component. The mold may include a mold body having a first sidewall, a second sidewall, and a bottom. The first sidewall, the second sidewall, and the bottom may each at least partially define a recess for receiving an antibiotic-impregnated material. The recess may extend continuously from the first sidewall through the bottom to the second sidewall. The recess may include two depressed outer arched sections that are spaced apart from each other by an inner section. The outer arched sections may be transverse to a longitudinal axis of the mold. The inner section may include a keel that extends upward from the bottom of the mold body and that has a height that set a size of a femoral component produced using the mold. The keel may include one or more calibration markings that indicate increments of adjustments to the size of the femoral component.

In some embodiments, a junction formed between the first sidewall and the bottom may include a breakaway feature that enables the first sidewall to be removed from the bottom. The breakaway feature may include one or more detents. A junction formed between the second sidewall and the bottom may include a breakaway feature that enables the second sidewall to be removed from the bottom. The one or more calibration markings may enable a user to accurately modify a height of the keel without further measurement. The one or more calibration markings may include multiple markings at equal intervals. The height of the keel may be between about 5 mm and 15 mm.

Embodiments of the present technology may encompass a femoral component kit. The kit may include a piston having a piston body. The piston body may include a notch formed in a bottom surface of the piston body. The kit may include a femoral component mold. The mold may include a mold body having a first sidewall, a second sidewall, and a bottom. The first sidewall, the second sidewall, and the bottom may each at least partially define a recess for receiving an antibiotic-impregnated material. The recess may extend continuously from the first sidewall through the bottom to the second sidewall. The recess may include two depressed outer arched sections that are spaced apart from each other by an inner section. The outer arched sections may be transverse to a longitudinal axis of the mold. The inner section may include a keel that extends upward from the bottom of the mold body. A height of the keel and a depth of the notch may set a size of a femoral component produced using the mold. The keel may be aligned with the notch when the piston is inserted within the femoral component mold. One or both of the notch and the keel may include one or more calibration markings that indicate increments of adjustments to the size of the femoral component.

In some embodiments, the piston may include a handle that is coupled with a top surface of the piston body. The handle may be spaced apart from the piston body. The kit may include a preformed tibial component. The preformed tibial component may include polyethylene. The kit may include a container of a bone cement powder. The kit may include a container of a liquid monomer.

BRIEF DESCRIPTION OF THE DRAWINGS

A further understanding of the nature and advantages of various embodiments may be realized by reference to the following figures. In the appended figures, similar components or features may have the same reference label.

FIG. 8 illustrates the placement of the bone cement into a mold.

FIG. 9 illustrates how the bone cement is formed in the mold.

DETAILED DESCRIPTION OF THE INVENTION

Figure 1:
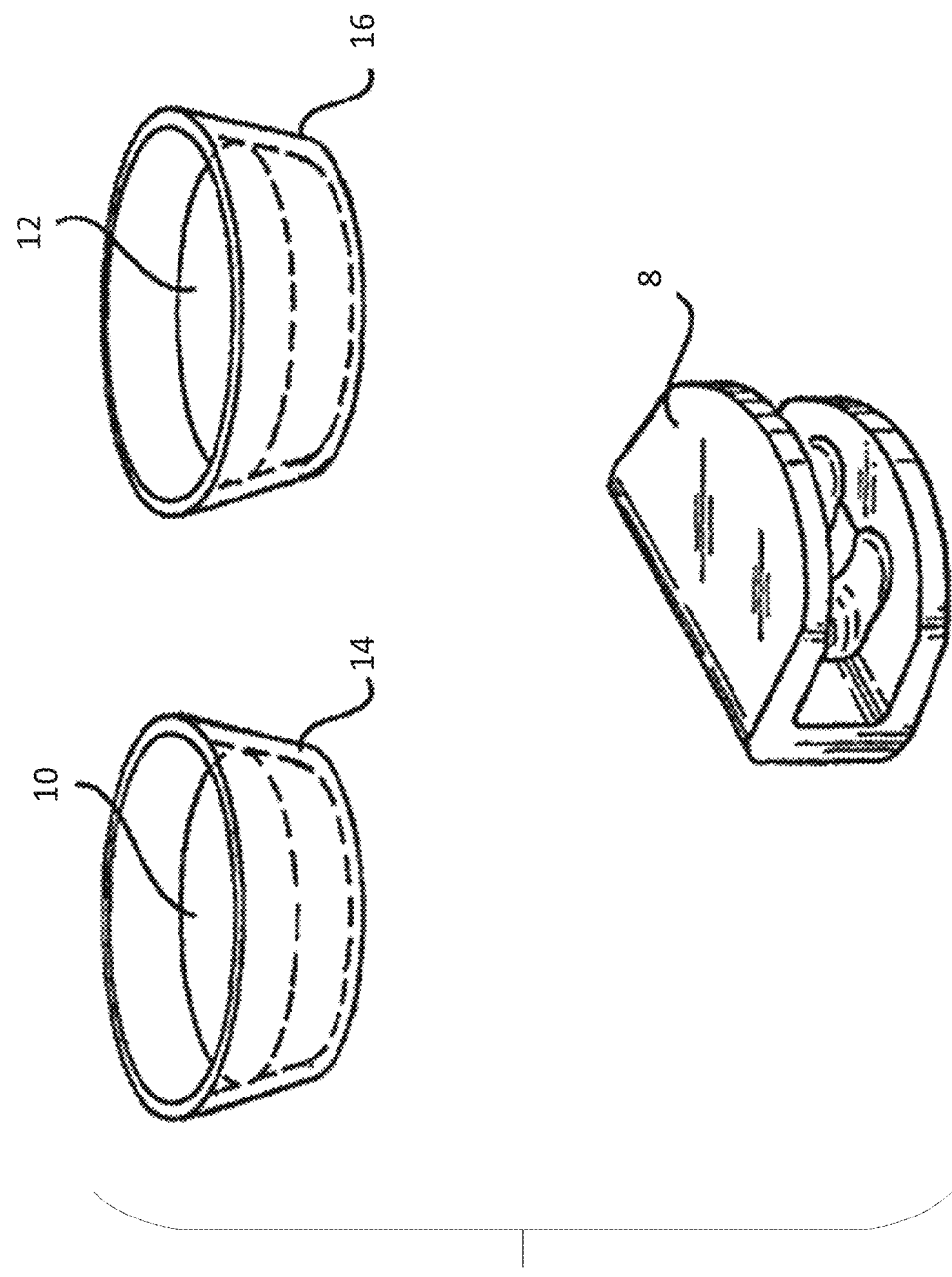
FIG. 1 illustrates a kit that may be used to make a femoral component when treating an infected area associated with a total knee replacement according to the invention.

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

The invention provides exemplary techniques and kits that may be used to treat an infected implant area resulting from a total knee replacement procedure. Following diagnosis of the infection, the implant area needs to be surgically accessed. This may be accomplished by forming a long incision on the front of the knee to expose the previously inserted femoral and tibia prostheses that form the knee replacement. This incision is typically through the scar of the original component implantation procedure. All infected total knee replacement implants, hardware are removed and a radical soft and hard tissue debridement is performed.

The implants are replaced with temporary implants that are used to fight the infection. One of the implants may be constructed of bone cement impregnated with an antibiotic while the other is made of a material that interfaces with the bone cement implant without causing excessive wear of the bone cement implant. This may be done during the surgical procedure to permit the surgeon to determine the proper size of the implant while the femur and the tibia are exposed. Both implants are fabricated and sized from matched size disposable calibrated mold that fabricates component which restores flexion extension gap sizing and joint line position in order to maximize joint range of motion and stability. The sized fabricated femoral and polyethylene tibial implants may be temporarily attached to the femur and the tibia using the antibiotic impregnated bone cement to help fight the infection. In so doing, the bone cement is allowed to sufficiently cure or harden so that the cement does not excessively interdigitate with the bone when the temporary components are inserted. Thus, when the implants are subsequently removed, the bone cement will not tear away excessive bone and other tissue. Also, the correctly sized implants are configured in a shape that permits movement of the leg at the knee joint while also providing stability, posterior as well as medial and lateral. This permits stable maximal movement in the leg to help prevent the leg from stiffening up while the temporary implants are in place. Once the infection has been treated, the knee is again opened, the temporary implants are removed and permanent revision knee replacement implants are put back in. As just described, by allowing the bone cement to somewhat harden before attaching the implants to the femur and the tibia, the implants may easily be removed without damaging the tissue and preserving the bone stock needed to perform adequate revision implantation of permanent components. In this way, the new revision knee replacement prosthetics may more easily be attached and implanted, thereby reducing length of surgery, and improving the final outcome per standard total joint replacement analysis.

The amount of antibiotics in preformed components is limited to the FDA approved single antibiotic low dose concentration available in commercially available antibiotic cement that is used for prophylaxis. Not enough antibiotic is in the cement for treatment of established infection even with intravenous antibiotics. In order to overcome this preformed low antibiotic dose dilemma, this method provides surgeon customization of the type and amount of treatment level antibiotic in the cement depending on the infecting organism and includes the ability to accurately restore flexion extension gaps and full range of motion. By using bone cement that includes a customizable type and amount of antibiotics, the antibiotic may elute from the bone cement at higher levels than can be obtained from the standard and simultaneous intravenous antibiotic administration that is administered routinely for four to six weeks. The antibiotics eluted from the bone cement also penetrate and treat avascular tissue that intravenous antibiotics cannot reach, thus increasing the overall success rate of the two-stage treatment over a simple one stage exchange of components. Such a mold provides the appropriate geometrical shape of the femoral component that allows articulation and movement of the knee joint during the treatment period. Additionally, the femoral component made from such a mold provides a smooth femoral component which decreases friction of the femoral component and polyethylene surface of the tibial component articulation during movement during the treatment period. This smooth geometric shape formed by the mold allows a greater range of motion of the knee to be maintained during treatment and decreases friction of the components and therefore the wear debris of the femoral and tibial articulation during movement in the treatment period. This is desirable because the wear debris cannot often be entirely removed at the final stage of surgery and instead becomes a residual foreign body that may aggravate treatment of the infection or even become a focus of a new infection after the antibiotics have eluted from the cement debris.

In this way, the infection may be treated by local antibiotic elution from the cement as well as intravenous antibiotic elution while also providing movement of the leg at the knee joint. Such techniques may generally prevent the leg from stiffening and may preserve knee joint range of motion, thereby reducing pain during treatment and allowing more functional activity of daily living during the recovery time. This also improves the technical ease and success of the final operation of revision knee component implantation and the ultimate outcome of improved knee joint range of motion and overall function of the final knee replacement.

After the infection has subsided and determined to be infection free, the implant area may be re-accessed, and the femoral and tibial components may be removed and replaced with a permanent femoral prosthesis and a tibial prosthesis. Because the bone cement was allowed to partially cure prior to implantation, the components may easily be removed.

In this embodiment the standard revision total knee instrumentation of the selected type, brand or model scheduled for the final second stage revision knee replacement may be used in published fashion to, 1) debride all infected bone, 2) prep the knee for the final second revision stage and, 3) to determine femoral augments and tibial component height measurements required to restore the joint line position and equal flexion and extension gaps. Once sequential debridement and joint line and gap position measurements are acquired, calibrations on each mold may be used to select and fashion a correctly sized U-shaped mold and femoral piston segments that will fabricate a correctly sized femoral cement component.

Antibiotic impregnated bone cement pancake is prepared and placed into the calibrated U-shaped segment. Then the piston segment of the two-piece mold is pushed into the cement loaded U-shaped side of the mold to the predetermined measured depth that restores the opposite side of the joint line. Extruded excess cement is removed and once the cement is nearly completely hardened/cured it is then removed from the breakaway U-shaped mold. This technique and two-piece mold provide restoration of the appropriate geometrical shape of the femoral component that includes replacement of the infected bone and cement, restoration of the joint line and flexion and extension gaps that in turn allows full range of motion without contracture or instability of the knee joint during the treatment period.

The closer to normal motion that can be achieved during treatment is directly proportional to the ease and result of the final reconstruction. Previous attempts at treatment of infected knee prosthesis with articulated temporary components have ignored the well-established principles of restoring joint line position and flexion and extension gaps that are required for every successful primary and revision knee replacement surgery. Consequently, restoration of the joint line and flexion and extension gaps required in every knee replacement surgery are not able to be addressed and restored, full range of motion is not achieved, extension and flexion contracture and/or instability are the end result.

The femoral component mold may be part of a kit that also includes a tibial component that is made of a smooth material, such as a polyethylene, to prevent wear and debris of the cement femoral component. A posterior stabilized polyethylene (or other smooth material) tibial component configuration adds knee joint stability to improved knee motion during treatment and prevents metal from being reintroduced into the joint as in a one stage reconstruction, which will aggravate treatment of the infection. (https://journals.lww.com/clinorthop/toc/2005/10000. THE CLASSIC: The Effect of Wound Environment on the Incidence of Acute Osteomyelitis. Evans, Richard P MD; Nelson, Carl L MD; Harrison, Barry H MS; Sherk, Henry H MD.). By restoring the knee joint line and flexion extension gaps, full range of motion without extension contracture or flexion instability becomes possible, predictable, and reproducible.

Referring now to the figures, one exemplary method for performing such a procedure will be described. In FIG. 1, an incision has already been made in the patient's knee and the knee joint implants have been removed. Prior to the removal of the joint implants being removed, the size of the infected femoral implants may be matched to the size of the mold selected and the size of the tibial polyethylene component is matched to the one removed. Measurements of the position of prior knee prostheses may be made. As just one example, a k-wire and/or bovie mark may be used to establish a random mark on the distal end of the femur just proximal to the existing femoral component. Measurement from this mark to the joint surface may be reproduced with the fabricated cement femur implant. Similar marks and/or measurement techniques may be reproduced for the tibial side replacement. After the joint implants, dead bone, and cement have been removed from femoral and tibial sides of the joint, both measurements may be re-made to determine the calibrated size of molded femoral component and thickness of the polyethylene tibial component required to fabricate a size of femoral component needed to restore the patient's flexion-extension gap and joint line position. After measurements have been taken, the temporary femoral component may be ready to be produced using a mold 8. This process utilizes an antibiotic impregnated material. The antibiotic material may include one or more antibiotics. In a particular embodiment, the antibiotic material may include two antibiotics 10 and 12 that are stored within containers 14 and 16. For example, agent 10 may include one kind of antibiotic while component 12 may include another kind of antibiotic. Conveniently, agent 10 may include powdered tobramycin, and agent 12 may include powdered vancomycin, commercially available from several pharmaceutical companies. However, it will be appreciated that based on infecting organism identified, the surgeon may choose other types of antibiotics may be used as well if they are heat stable, elute from the bone cement and are desired to more specifically treat a given infectious organism that has been identified.

Figure 2:
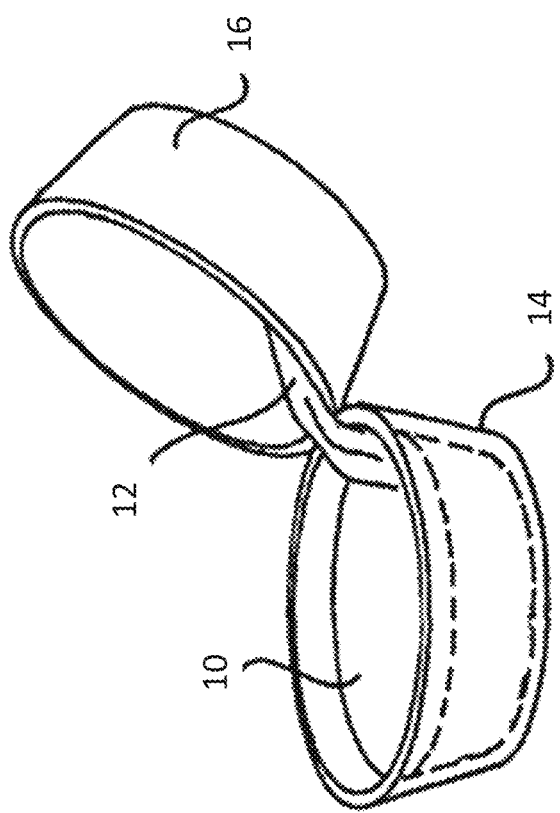
FIG. 2 illustrates a method for dividing an antibiotic/bone cement powder according to the invention.

As shown in FIG. 2, agents 10 and 12 are combined and powdered bone cement is also added. Often the antibiotics obtained are granular and may be made into a finer powder once again by pushing the powder through a standard commercially available cement screen. These are mixed with the bone cement, which may also in powder form. In some embodiments, the bone cement may include a methylmethacrylate polymer, commercially available from a number of companies. It should be stated that Palacos type of bone cement, commercially available from many manufacturers has been shown to have the best antibiotic elution characteristics by a number of studies and is the preferred bone cement to use, although other forms of bone cement may be used in various embodiments.

Figure 3:
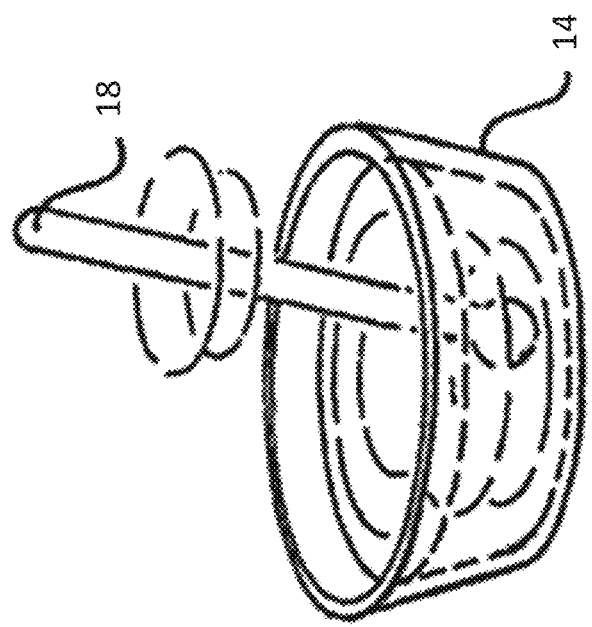
FIG. 3 illustrates a method for mixing the antibiotic with the bone cement.

The bone cement and antibiotic(s) are mixed together, such as by using a stirrer 18 as shown in FIG. 3. In some embodiments, the mixture may then be divided by placing half back into container 14 for later use as described hereinafter. In other embodiments, the entire mixture may be used for fabricating the femoral component and a separate batch of bone cement may be mixed to secure the femoral component and/or tibial component in place to form the patient's temporary knee.

Figure 4:
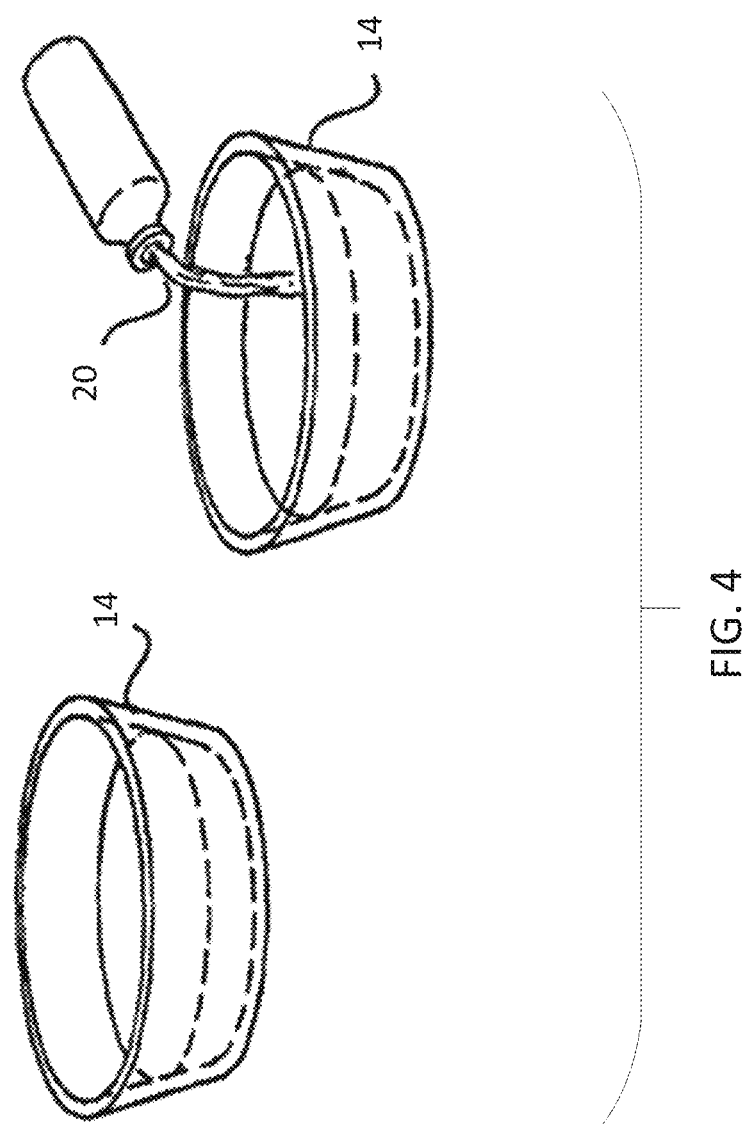
FIG. 4 illustrates a method for adding an activating agent to the antibiotic/bone cement mixture.

In FIG. 4, a liquid activating agent 20 (e.g., a monomer universally provided with each bone cement kit from all companies) is added to the mixture. The activating agent 20 may react with the bone cement powder to form polymethylmethacrylate 22 (also referred to as PMMA).

Figure 5:
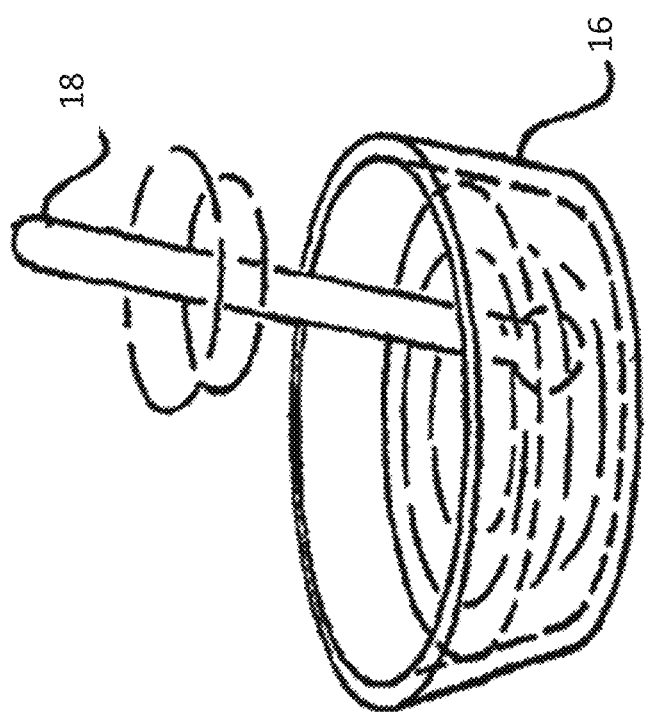
FIG. 5 illustrates a method for mixing the activating agent with the bone cement mixture.

The mixture is stirred with stirrer 18 until the PMMA 22 has a doughy consistency as shown in FIG. 5. Although described using one type of bone cement with specific types of antibiotics, it will be appreciated that other bone cements and antibiotic agents may be used in place of or in addition to PMMA, including those described in U.S. Pat. No. 6,355,705, the complete disclosure of which is herein incorporated by reference.

Figure 6:
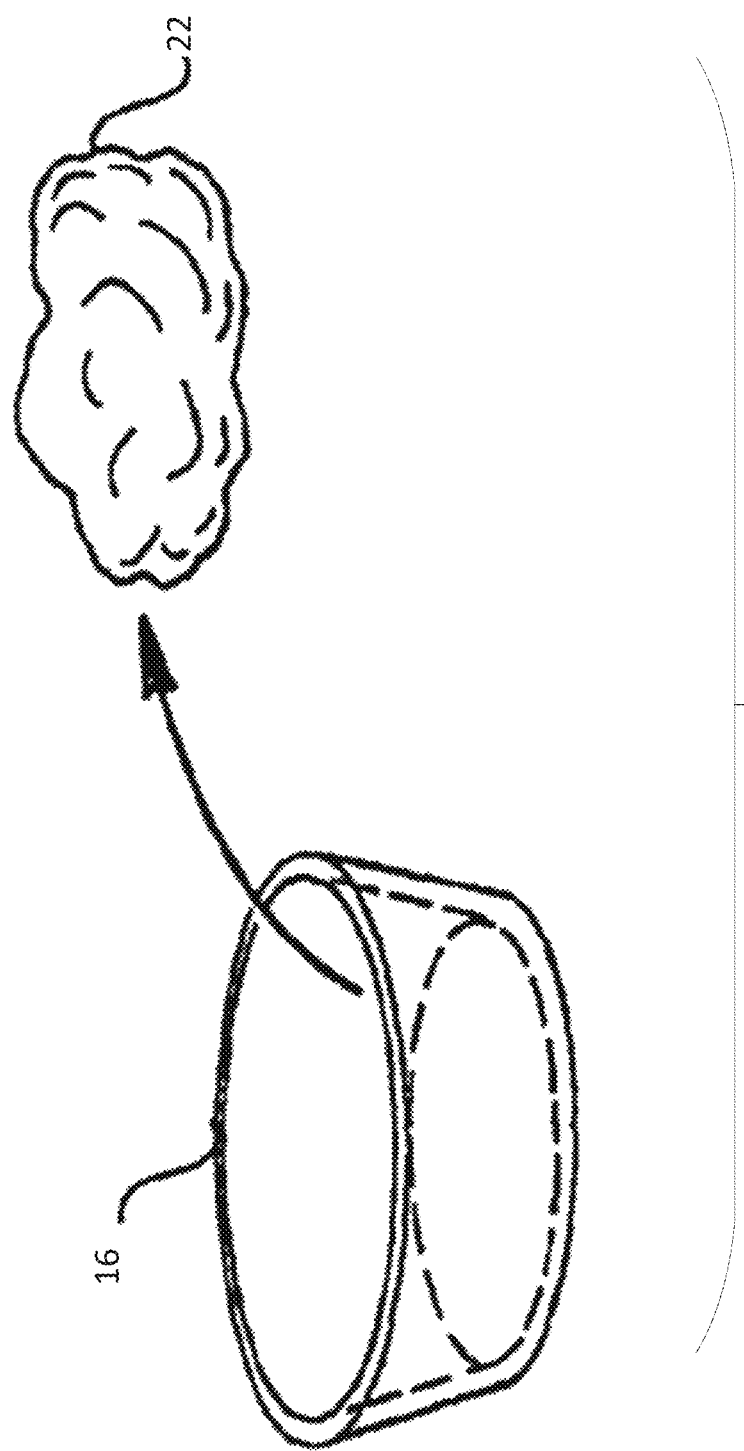
FIGS. 6 and 7 illustrate a method for shaping the resulting bone cement.
Figure 7:
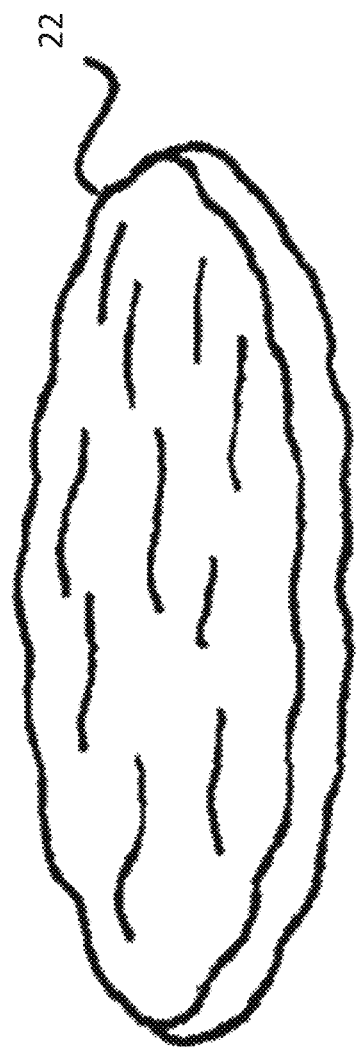

In FIG. 6, the PMMA 22 may be removed from container 16 and formed into a pancake shape as shown in FIG. 7. The PMMA 22 is then placed into mold 8 as shown in FIG. 8. Mold 8 may include a mold body having a pair of sidewalls 24 and 26 and a bottom 28. Mold 8 may be constructed of a flexible material, such as a medical grade plastic, to permit sidewalls 24 and 26 to be flexed away from each other. In some embodiments, mold 8 may be a breakaway mold to facilitate removal of the resulting fabricated femur component 40. For example, the mold body may include one or more breakaway features 80 that may be formed at a junction between the first sidewall 24 and the bottom 28 and/or at a junction between the second sidewall 26 and the bottom 28. The breakaway features 80 may include detents, perforations, slits, thin areas, and/or other mechanical features that may facilitate easy flexing and/or separation of one or both sidewalls 24, 26 of the mold from the bottom 28. In some embodiments, one or more breakaway features may be formed at other areas of the mold body other than, or in addition to, at junctions of one or both sidewalls 24, 26 and the bottom 28. For example, one or more breakaway features may be disposed on the bottom 28 and or one or both of the sidewalls 24, 26 that permit the respective component of the mold body to be flexed and/or separated from the rest of the mold body to facilitate easy removal of the femoral component from the mold 8.

Formed in mold 8 is a recess 30 that is in the shape of the exterior of a traditional femoral prosthesis 15 modified (thickened throughout) to provide greater strength to the cement femoral component. As shown, recess 30 includes two depressed two outer arched sections 32 and 34 and an inner section 36, which are each partially defined by the first sidewall 24, second sidewall 26, and bottom 28. For example, the recess may extend continuously from the first sidewall 24 through the bottom 28 to the second sidewall 26 to define a surface of the femoral component that interfaces with a tibial component. The inner section is vertically below the bottom of the U-shaped back surface such that the center section of the resulting femoral component is formed when the antibiotic-impregnated material is placed into the recess 30. The two outer arched sections 32 and 34 are transverse to the sidewalls 24 and 26 and a longitudinal axis of the mold. As best illustrated in FIG. 9b, the inner section 36 may include a keel 38 that extends upward from the bottom 28 of the mold body. The keel 38 may have a generally rectangular cross-section (possibly with rounded edges and/or corners) and may be centered within the inner section 36. The keel 38 may have a height that determines a final thickness of the femur that is used to set a size of a flexion-extension gap for the femoral component produced using the mold 8. For example, the height of the keel 38 may determine a thickness of the femoral component, which may determine the size of a flexion-extension gap and/or joint line position of the knee prosthesis assembly. Based on the measurements of the patient's flexion-extension gap and joint line, the height of the keel 38 may be modified to generate a femoral component that restores the patient's original flexion-extension gap and joint line. For example, the keel 38 may be trimmed or otherwise resized to a shorter height, which may result in a thinner femoral component being fabricated using the mold 8. To better facilitate the resizing of the keel 38, the keel 38 may include one or more calibration markings 62, which may enable a user to accurately modify a height of the keel without further measurement. The calibration markings 62 may be formed on one or more lateral surfaces of the keel 38, and may each designate a different calibration height to generate a femoral component of a particular size that will accurately restore the flexion-extension gap and joint line of the patient's knee. In some embodiments, the calibration markings 62 may be positioned at equal intervals, such as at every 1 mm, every 5 mm, and/or other interval. For example, a height of the keel 38 may be 15 mm, with calibration markings 62 indicating heights of 5 mm and 10 mm. In other embodiments, other intervals, possibly including irregular intervals may be utilized. The calibration markings 62 may be superficial markings (such as using ink, dye, etc.), notches that extend into a lateral surface of the keel 38, protrusions (such as embossed lines and/or other protruding effects), and/or other markings. Oftentimes, an initial height of the keel 38 may be between about 5 mm and 20 mm, or between about 5 mm and 15 mm, although other initial heights are possible. The keel 38 may be cut down to any lower height (including 0) that is necessary to generate a femoral component that restores the patient's original flexion-extension gap and joint line. In some embodiments, the reduced height may correspond to one of the calibration markings 62, while in other instances the reduced height may be above or below one or more of the calibration markings 62. For example, if the calibration markings 62 are provided at 5 mm intervals, a user may trim or otherwise reduce the height of the keel 38 between the 5 mm and 10 mm calibration mark 62.

Mold 8 may be used to produce a femoral component 40 that interfaces with a tibial component 42 as described hereinafter (see FIG. 12). However, it will be appreciated that other shapes of femoral components may be produced as well, including those known in the art and those described in U.S. Pat. Nos. 5,226,915 and 6,506,215, the complete disclosures of which are herein incorporated by reference.

Figure 9A:
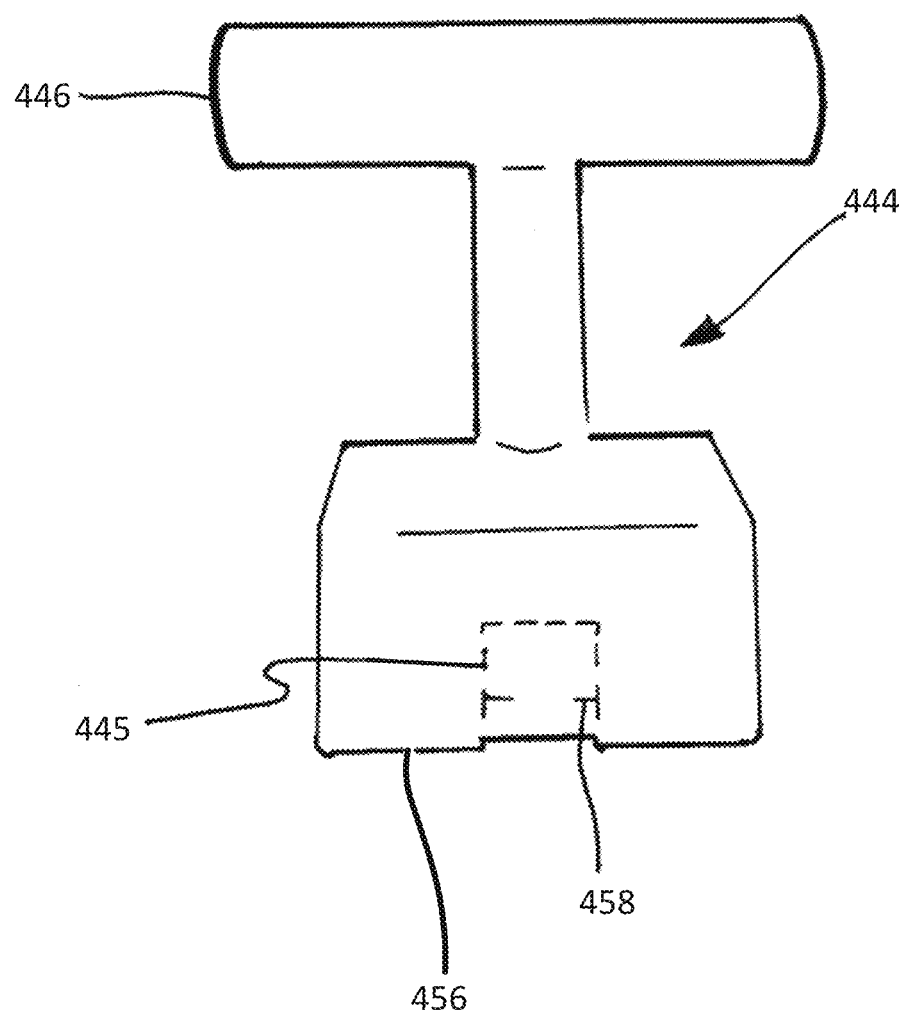
FIG. 9a illustrates anterior view of femoral piston mold with notch calibration.
Figure 9B:
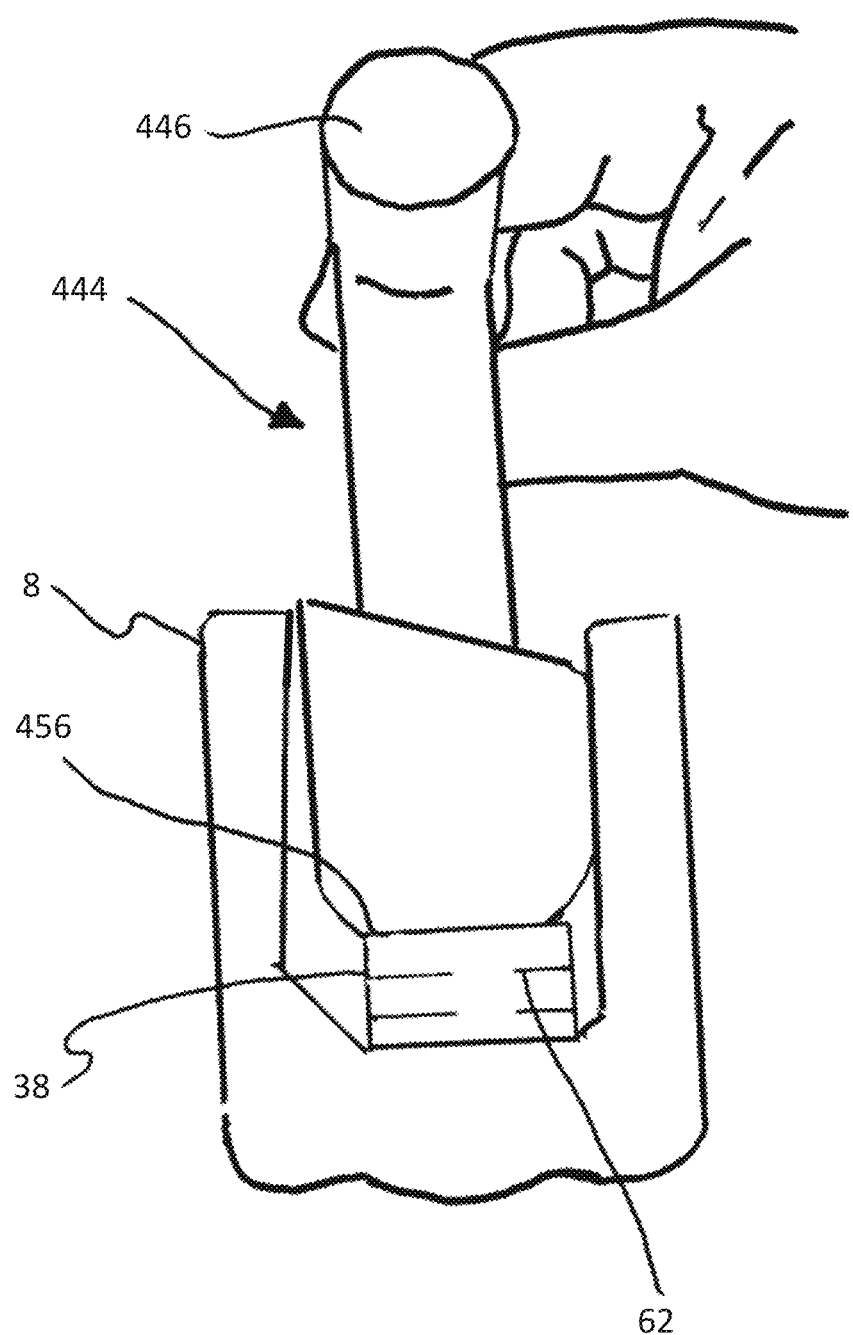
FIG. 9b illustrates lateral view femoral piston mold engaged with U-shaped breakaway mold showing calibrated spine.

As shown in FIG. 9, the PMMA 22 may be pressed into recess 30 with a straight edge 44 used to smooth the back side of the PMMA 22 into the U-shaped mold 8. In other embodiments, rather than, or in addition to, using the straight edge 44, a piston 444 may be used to press the PMMA 22 into the recess 30. FIG. 9a illustrates anterior view of a one-piece piston 444 having a T-shaped handle (although other pistons may have no handle or a different handle and/or may be formed from multiple pieces) and FIG. 9b illustrates a lateral view of the piston 444 inserted within mold 8. Piston 444 may include a piston body that is sized to fit within an interior of the mold 8. A handle 446 may extend from the piston body, with the handle 446 being spaced apart from the piston body.

In some embodiments, a bottom surface 456 of the piston body may include calibrations that define a notch 445 (while in other embodiments a bottom surface 456 of the piston body may be generally flat). Notch 445 may extend upward into a center portion of the piston body aligned with the keel 38. In some embodiments, the notch 445 may be generally rectangular in shape. For example, the notch 445 may have a uniform depth that extends from a first edge of the bottom surface 456 to a second opposite edge of the bottom surface 456. In other embodiments, the notch 445 may be generally U-shaped, such that a portion of the notch 445 forms an indented region that extends upward along at least a portion of one or more of the lateral sides of the piston body. A depth of the notch 445 may be up to about 20 mm. Oftentimes, a depth of the notch 445 may be between about 5 mm and 15 mm. In some embodiments, the depth of the notch 445 may be modified to generate a femoral component that restores the patient's original flexion-extension gap and joint line. For example, the notch 445 may be trimmed or otherwise resized to a greater depth, which may result in a thinner femoral component being fabricated using the mold 8. To better facilitate the resizing of the notch 445, one or more lateral sides of the piston body may include one or more calibration markings 458 that may be positioned above the current notch 445, which may enable a user to accurately modify a depth of the notch 445 without further measurement. The calibration markings 458 (best illustrated in FIG. 9a) may be formed on one or more lateral surfaces above the notch 445, and may each designate a different calibration depth to generate a femoral component of a particular size that will accurately restore the flexion-extension gap and joint line of the patient's knee. In some embodiments, the calibration markings 458 may be positioned at equal intervals, such as at every 1 mm, every 5 mm, and/or other interval. For example, a depth of the notch 445 may be 5 mm, with calibration markings 62 indicating depths of 10 mm and 15 mm. In other embodiments, other intervals, possibly including irregular intervals may be utilized. The calibration markings 458 may be superficial markings (such as using ink, dye, etc.), notches that extend into a lateral surface of the piston body, protrusions (such as embossed lines and/or other protruding effects), and/or other markings. In some embodiments, an increased depth may correspond to one of the calibration markings 458, while in other instances the increased depth may be above or below one or more of the calibration markings 458.

Figure 9C:
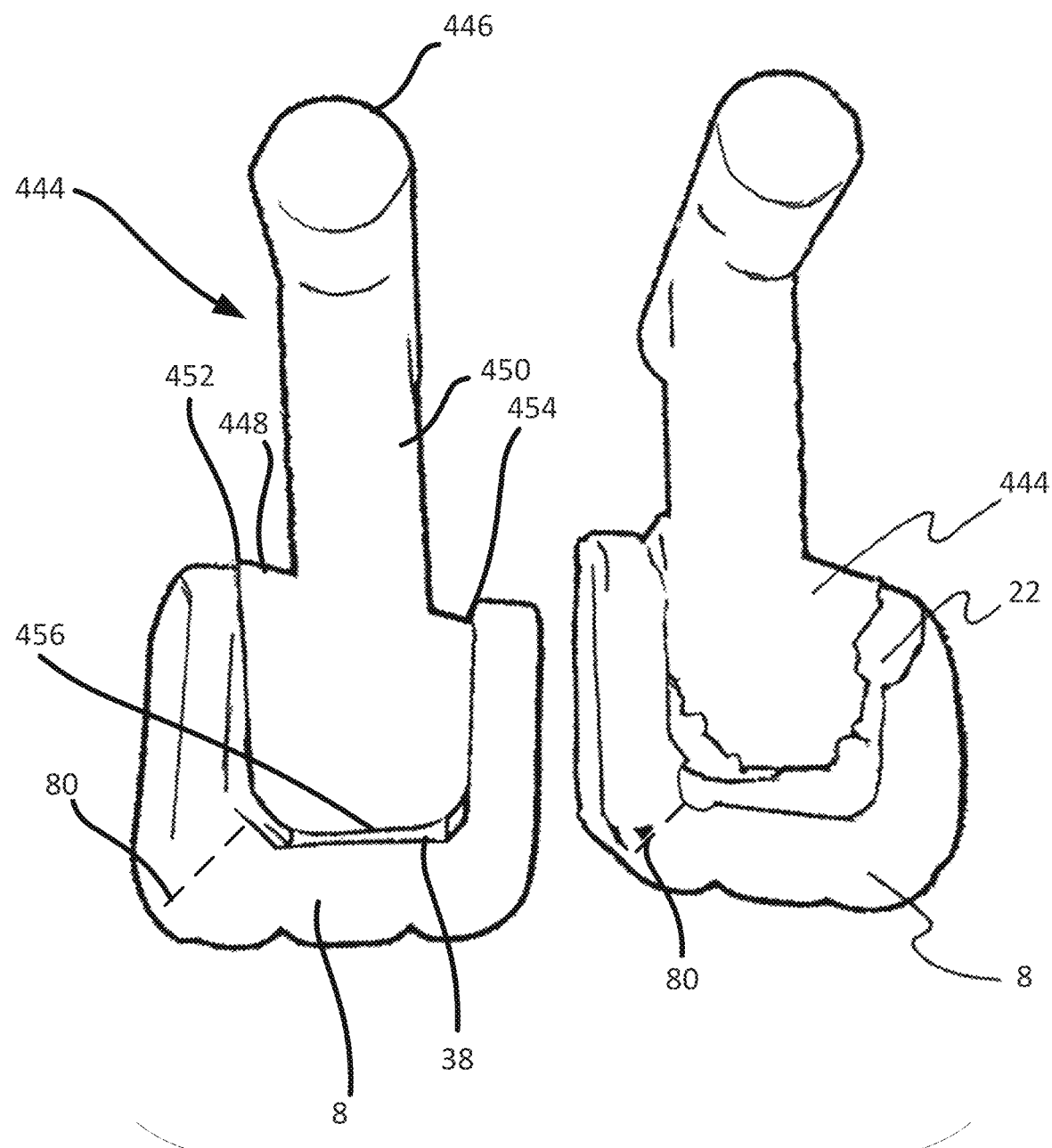
FIG. 9c illustrates the two-piece femoral piston articulation with the U-shaped mold without cement and with molded cement.

The depth of the notch 445, along with a height of the keel 38, may control an insertion or compression depth of the piston 444, which may control a final calibrated thickness of the femoral component 40. For example, as shown in FIG. 9c, when the piston 444 is inserted within the mold 8, the notch 445 may be aligned with the keel 38 such that the contact between a bottom surface of the notch 445 and a top surface of the keel 38 may limit the insertion depth of the piston 444 to set the thickness of the resultant femoral component 40. This enables the thickness and size of the fabricated cement component to replicate the same size and thickness as the removed femoral component and infected bone, thereby ensuring that the amount of flexion-extension gap provided by the knee prosthesis assembly properly restores the patient's original joint mechanics. For example, a deeper notch 445 and/or a shorter keel 38 may reduce the thickness of the femoral component 40, while a shallower notch 445 and/or a taller keel 38 may increase the thickness of the resultant femoral component 40. In operation, a user may determine what combination of keel height and notch depth are necessary to restore the patient's flexion-extension gap and joint line position. Upon making this determination the keel 38 and/or notch 445 may be trimmed and/or otherwise altered to produce a combination of keel and notch sizes that will properly restore the patient's flexion-extension gap and joint line position.

Figure 10:
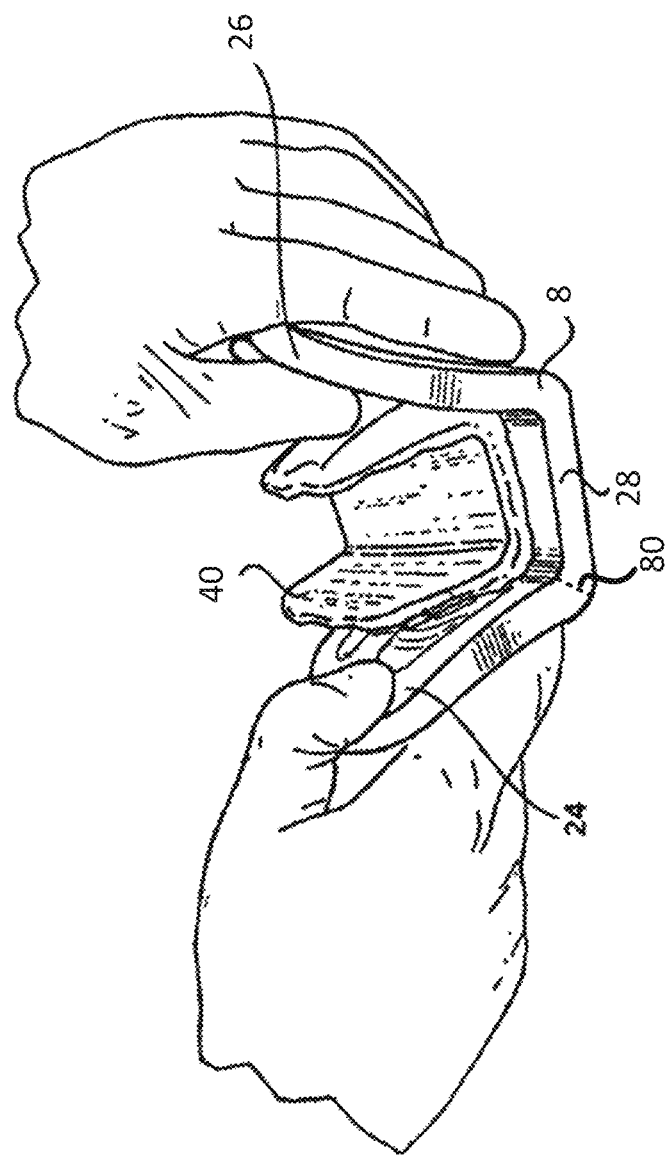
FIG. 10 illustrates the removal of the resulting femoral component from the mold.

Once formed in the desired shape and thickness, the femoral component 40 is removed and sidewalls 24 and 26 of the U-shaped mold 8 are pulled away from each other as shown in FIG. 10 to permit the femoral component 40 to be removed from mold 8. Mold 8 can be breakaway design to facilitate removal. For example, the breakaway features 80 may be used to separate the first sidewall 24 and/or second sidewall 26 (and/or portions thereof) from the bottom 28 to more easily enable the femoral component 40 to be removed from mold 8.

Figure 11:
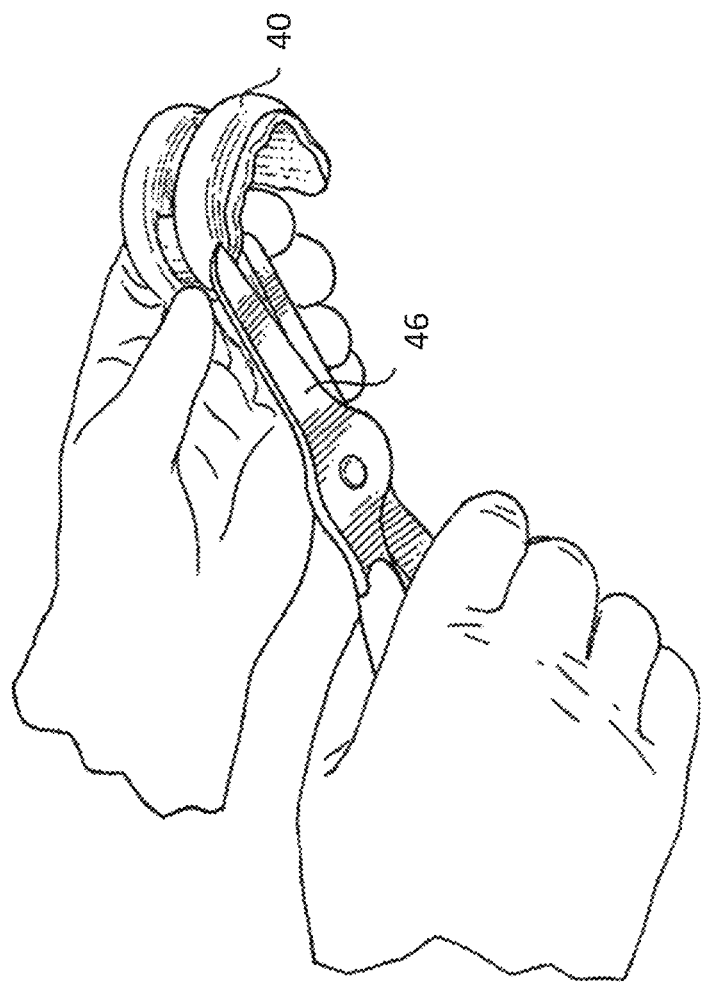
FIG. 11 illustrates the removal of excess material from the femoral component.

When removed from mold 8, femoral component 40 is still somewhat soft and allows any unwanted edges to be trimmed using scissors 46 as shown in FIG. 11. The approximate time from mixing to removal from the mold 8 is about three minutes to about ten minutes depending on the type of cement used, the amount and type of antibiotics mixed into the cement and the room temperature. Femoral component 40 is typically hard enough to be attached to the femur after about five minutes to about fifteen minutes from the time of mixing.

Figure 12:
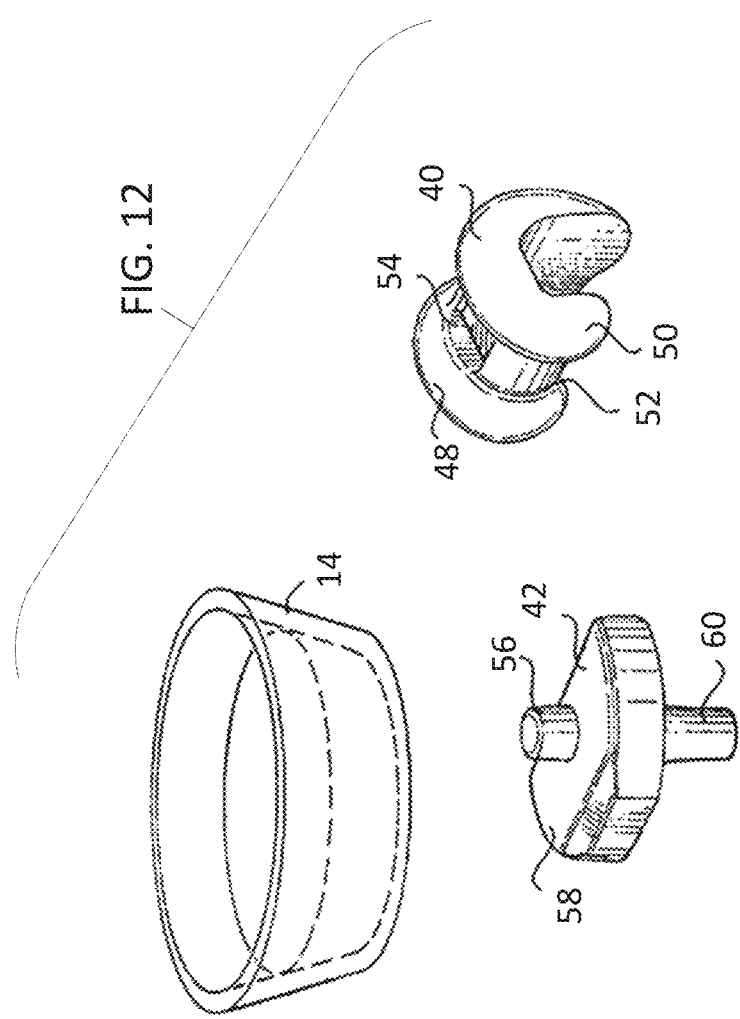
FIG. 12 illustrates the femoral component of FIG. 11 along with a tibial component.

As best shown in FIG. 12, femoral component has two outer rails 48 and 50 (which correspond to depressed two outer arched sections 32 and 34) and a center section 52 (which corresponds with inner section 36). Formed in center section 52 is a recess 54 (which corresponds with keel 38) for receiving the posterior stabilizing protrusion 56 of a tibial component 42. Tibial component 42 may be a one-piece all-polyethylene (or other polymer) component from a manufacturer of choice which incorporates a tray 58 and a central stem 60 that fits within the tibia. In use, protrusion 56 fits within recess 54 and rails 48 and 50 sit on tray 58.

In this way, femoral component 40 and tibial component 42 may articulate with respect to each other while providing posterior as well as lateral and medial stability to the knee joint. Tibial component 42 may also be constructed of a material that will not cause excessive wear on femoral component 40. Examples of materials include polymer materials, such as polyethylene. Hence, when the two components are interfaced with each other, the knee joint may articulate without degrading or breaking the relatively fragile femoral component 40. This permits the patient to be able to articulate the leg while the infection is being treated.

Figure 13:
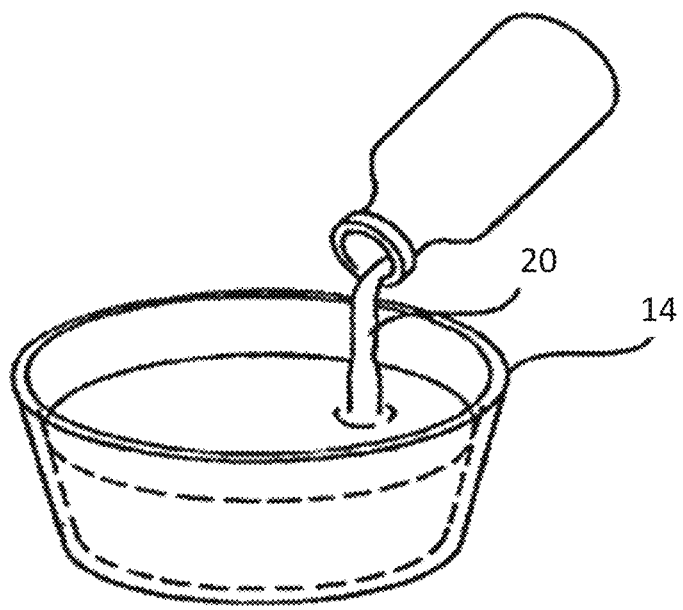
FIGS. 13 and 14 illustrate a method for making more antibiotic impregnated bone cement.
Figure 14:
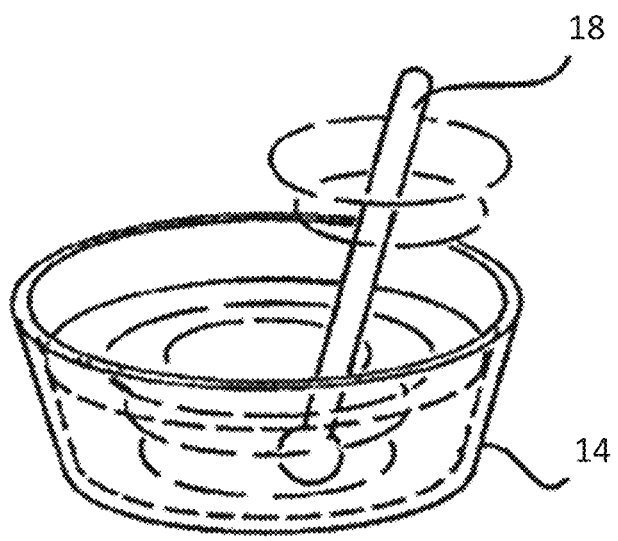

With femoral component 40 sufficiently hardened, the femoral component 40 may be ready to be attached to the femur. To do so, container 14 which holds the reserved half of the antibiotic-laden bone cement is combined with activating agent 20 as shown in FIG. 13. This is then mixed with stirrer 18 (see FIG. 14) in essentially the same was as previously described to provide more PMMA. At this point, timing is critical. The PMMA may be used both to attach tibial component 42 to the tibia and femoral component 40 to the femur. However, since both of these components will be removed once the infection has been treated (in about 6 to 12 weeks); they need to be cemented in such a way that they can be removed without causing significant tissue damage. As such, the PMMA 22 is allowed to cure to the point where it still has adhesive qualities, but yet does not provide excessive bonding or bone recess interdigitation so that the two prostheses may easily be removed and replaced with their permanent counterparts. Typically, the PMMA 22 will be used within a window of about two minutes to about five minutes after mixing again depending on the cement type used, the amount and type of antibiotics mixed into the cement and the room temperature.

Figure 15:
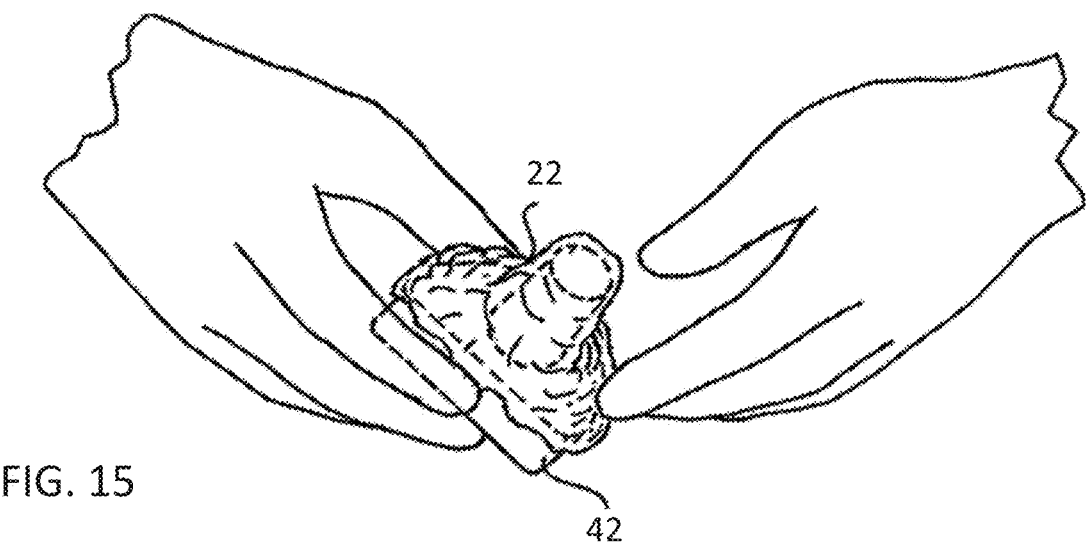
FIG. 15 illustrates a method for placing the bone cement onto the tibial component.
Figure 15A:
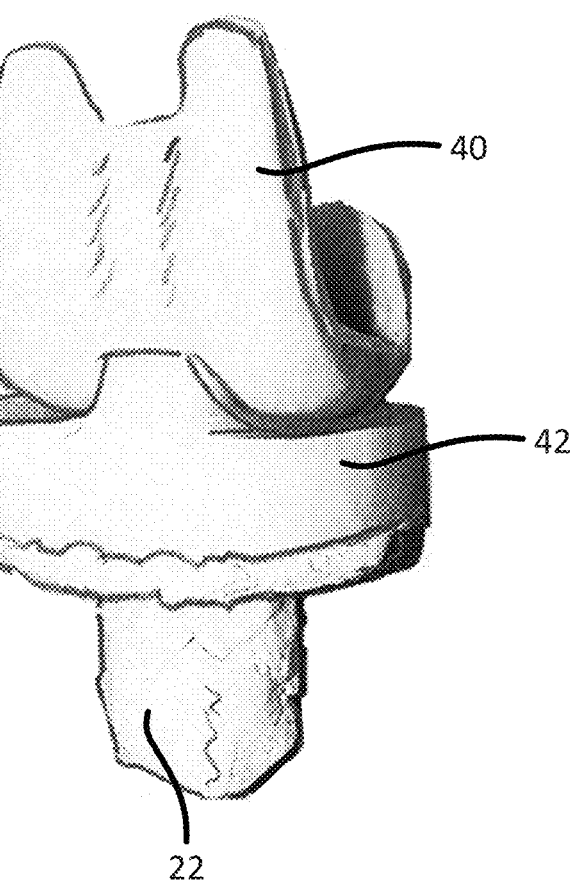
FIG. 15a illustration of cement placed on back of femoral component of FIG. 11 and inferior keel of the now articulating polyethylene tibial component of FIG. 15.

FIG. 15*a* is an assembled illustration of cement placed on back of femoral component of FIG. 11 and stabilizing protrusion 56 of the articulating tibial component 42 of FIG. 15 prior to implantation.

Figure 16:
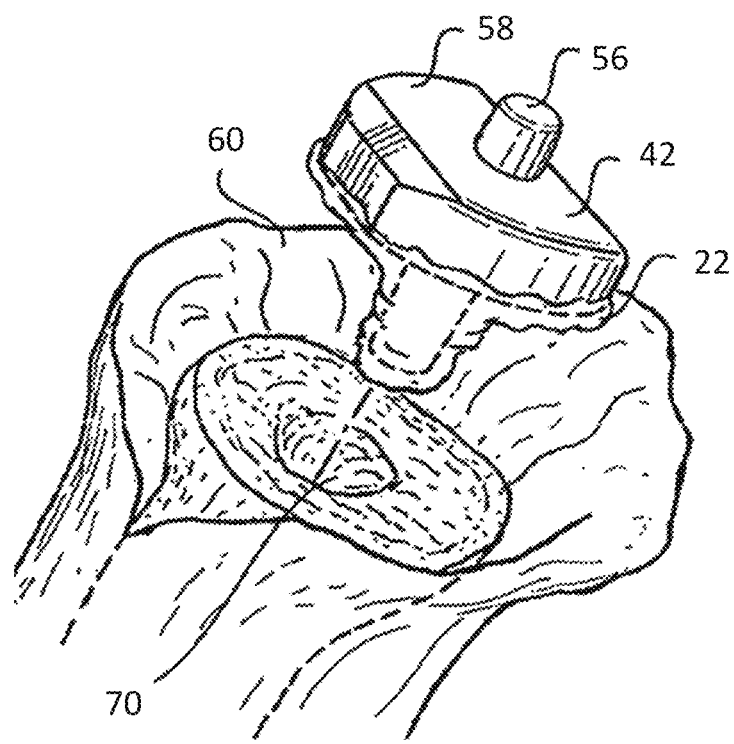
FIGS. 16 and 17 illustrate a method for inserting the tibial component into the tibia.
Figure 17:
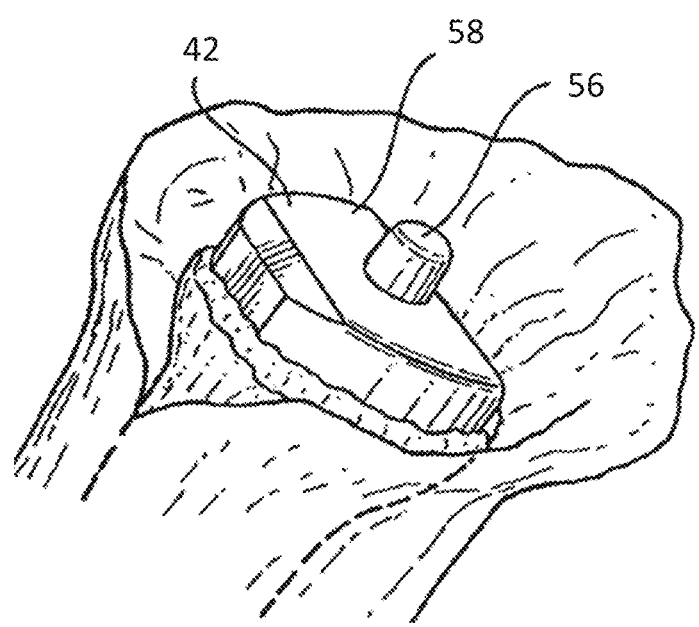

As shown in FIG. 15, the semi-cured PMMA 22 is formed around stem 60 and the bottom of tray 58 to a thickness of about one quarter inch to about one-half inch. At this point, the PMMA 22 is quickly setting and the surgeon is just able to form it around stem 60. As shown in FIGS. 16 and 17, tibial component 42 and the applied antibiotic cement are pressed into the tibia, with stem 60 extending into the intramedullary canal 70. Excess cement extrude during the insertion process is removed.

Figure 18:
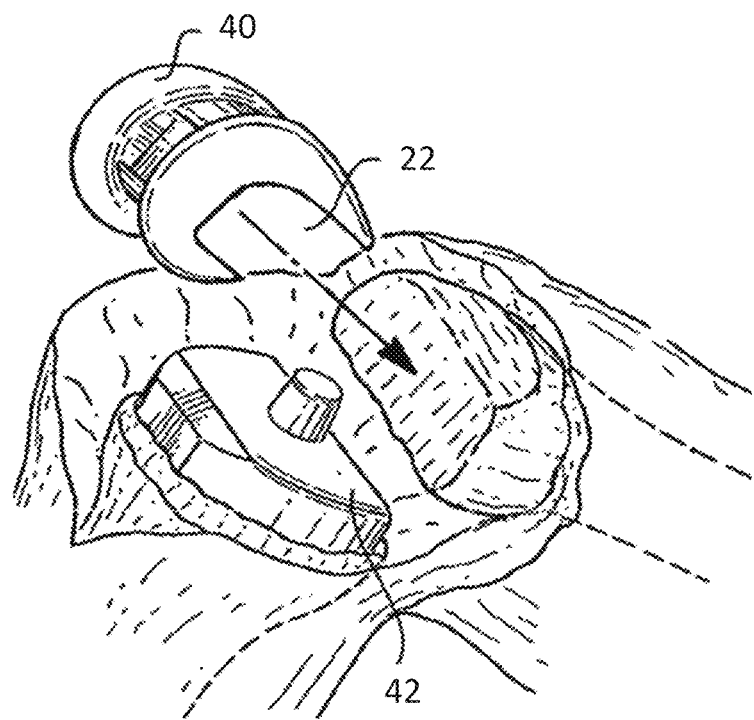
FIG. 18 illustrates a method for attaching the femoral component to the femur using bone cement.
Figure 19:
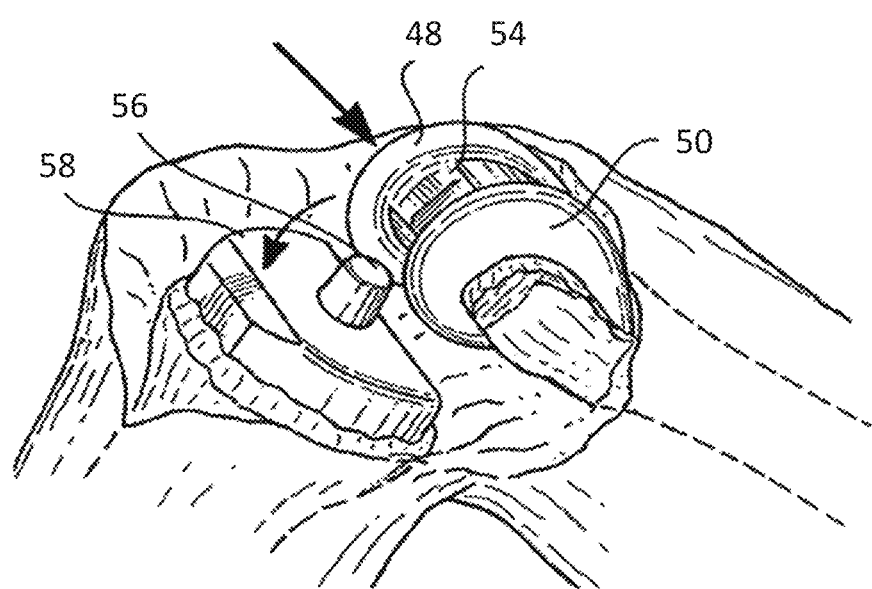
FIG. 19 illustrates the step of interfacing the tibial component with the femoral component.

More of the semi-cured PMMA 22 is also placed on the back side of femoral component 40 to a thickness of about one quarter inch to about one-half inch as shown in FIG. 18. Femoral component 40 is then placed over the bottom of the femur as shown in FIG. 19. The protrusion 56 is then immediately placed into recess 54 and the leg is straightened so that rails 48 and 50 may roll over tray 58. Excess cement extrudes during the insertion process is removed. The incision is then closed. The surgeon can and should move the knee prior to and after wound closure to ensure adequate articulation occurs as planned.

The patient should be able to and is encouraged to bend the leg at the knee and straighten it completely. This helps to prevent the buildup of scar tissue and the leg from stiffening. As previously described, the two components provide stability to the knee joint to facilitate its articulation and rehabilitation. The bone cement used to form the femoral component 40 as well as the bone cement used to attach the two components to the tibia and the femur leach out over time to fight the infection. Although the femoral component can withstand the weight of the patient's leg and forces concomitant to normal activities of daily living the cement femoral component adhesion may not be strong enough to withstand routine full weight bearing and the patient is discouraged to do so. Rather the patient uses ambulatory aides such as crutches or a walker until the second surgery when permanent components are implanted.

Once the infection has been treated, the knee may again be opened and the femoral component 40 and the tibial component 42 removed. As previously mentioned, the bone cement used to attach the two components to the bone was semi-cured, permitting the two components to easily be pulled from the bone without causing significant damage. The previously removed knee joint prosthesis may then be replaced with revision total knee components as is known in the art. Because little or no damage was caused by the temporary prostheses and because joint space and range of motion was maintained this process is relatively easy and comparable to a non-infected one stage revision knee replacement typically performed for component loosening or mechanical failure.

In some embodiments, a kit may be provided that includes one or more of the components described herein. For example, the kit may include the femoral component mold 8 and the piston 444. In some embodiments, the kit may also include one or more pre-formed tibial components, which may be sized to meet the patient's existing tibial structure. In some embodiments, the kit may include a container of a bone cement powder and/or a container of a liquid monomer.

The methods, systems, and devices discussed above are examples. Some embodiments were described as processes depicted as flow diagrams or block diagrams. Although each may describe the operations as a sequential process, many of the operations can be performed in parallel or concurrently.

In addition, the order of the operations may be rearranged. A process may have additional steps not included in the figure. It will be further appreciated that all testing methods described here may be based on the testing standards in use at the time of filing or those developed after filing.

It should be noted that the systems and devices discussed above are intended merely to be examples. It must be stressed that various embodiments may omit, substitute, or add various procedures or components as appropriate. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known structures and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate to in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate to in the context of the systems, devices, circuits, methods, and other implementations described herein.

As used herein, including in the claims, "and" as used in a list of items prefaced by "at least one of" or "one or more of" indicates that any combination of the listed items may be used. For example, a list of "at least one of A, B, and C" includes any of the combinations A or B or C or AB or AC or BC and/or ABC (i.e., A and B and C). Furthermore, to the extent more than one occurrence or use of the items A, B, or C is possible, multiple uses of A, B, and/or C may form part of the contemplated combinations. For example, a list of "at least one of A, B, and C" may also include AA, AAB, AAA, BB, etc.

What is claimed is:

1. A method for treating an infected area associated with a total knee replacement, comprising:
   providing a piston comprising a piston body, the piston body comprising a notch formed in a bottom surface of the piston body;
   providing a femoral component mold comprising:
      a mold body comprising a first sidewall, a second sidewall, and a bottom, wherein:
         the first sidewall, the second sidewall, and the bottom each at least partially define a recess that extends continuously from the first sidewall through the bottom to the second sidewall;
         the recess comprises two depressed outer arched sections that are spaced apart from each other by an inner section;
         the outer arched sections are transverse to a longitudinal axis of the mold;
         the inner section comprises a keel that extends upward from the bottom of the mold body;
         the keel is aligned with the notch when the piston is inserted within the femoral component mold; and
         one or both of the notch and the keel comprise one or more calibration markings that indicate increments of adjustments to a size of a femoral component formed using the femoral component mold;
   setting the size of the femoral component based on a measured flexion-extension gap and a measured joint line position of a prior knee structure, wherein the size of the femoral component is determined by a height of the keel of the femoral component mold and a depth of the notch in the piston;
   positioning bone cement within the recess of the femoral component mold;
   compressing the bone cement within the femoral component mold using the piston to form the femoral component; and
   removing the femoral component from the femoral component mold after the femoral component has at least partially set.

2. The method for treating an infected area associated with a total knee replacement of claim 1, further comprising:
   mixing a bone cement powder with a monomer and a surgeon-determined amount and type of one or more antibiotics to form the bone cement.

3. The method for treating an infected area associated with a total knee replacement of claim 1, further comprising:
   measuring the flexion-extension gap and the joint line position of the prior knee structure.

4. The method for treating an infected area associated with a total knee replacement of claim 1, further comprising:
   applying the femoral component to a femur of a patient.

5. The method for treating an infected area associated with a total knee replacement of claim 1, wherein:
the at least one marking is provided on the keel; and
setting the size of the femoral component comprises reducing the height of the keel to match one of the at least one marking on the keel.

6. The method for treating an infected area associated with a total knee replacement of claim 1, wherein:
the at least one marking is provided on the piston; and
setting the size of the femoral component comprises increasing a depth of the notch of the piston to match one of the at least one marking on the piston.

7. The method for treating an infected area associated with a total knee replacement of claim 1, wherein:
removing the femoral component from the mold comprises breaking the mold by disengaging the first sidewall from the bottom.

8. A mold for forming a femoral component, comprising:
a mold body comprising a first sidewall, a second sidewall, and a bottom, wherein:
the first sidewall, the second sidewall, and the bottom each at least partially define a recess for receiving an antibiotic-impregnated material, the recess extending continuously from the first sidewall through the bottom to the second sidewall;
the recess comprises two depressed outer arched sections that are spaced apart from each other by an inner section;
the outer arched sections are transverse to a longitudinal axis of the mold;
the inner section comprises a keel that extends upward from the bottom of the mold body and that has a height that set a size of a femoral component produced using the mold; and
the keel comprises one or more calibration markings that indicate increments of adjustments to the size of the femoral component.

9. The mold for forming a femoral component of claim 8, wherein:
a junction formed between the first sidewall and the bottom comprises a breakaway feature that enables the first sidewall to be removed from the bottom.

10. The mold for forming a femoral component of claim 9, wherein:
the breakaway feature comprises one or more detents.

11. The mold for forming a femoral component of claim 9, wherein:
a junction formed between the second sidewall and the bottom comprises a breakaway feature that enables the second sidewall to be removed from the bottom.

12. The mold for forming a femoral component of claim 8, wherein:
the one or more calibration markings enable a user to accurately modify a height of the keel without further measurement.

13. The mold for forming a femoral component of claim 8, wherein:
the one or more calibration markings comprise multiple markings at equal intervals.

14. The mold for forming a femoral component of claim 8, wherein:
the height of the keel is between about 5 mm and 15 mm.

15. A femoral component kit, comprising:
a piston comprising a piston body, the piston body comprising a notch formed in a bottom surface of the piston body; and
a femoral component mold, the femoral component mold comprising:
a mold body comprising a first sidewall, a second sidewall, and a bottom, wherein:
the first sidewall, the second sidewall, and the bottom each at least partially define a recess for receiving an antibiotic-impregnated material, the recess extending continuously from the first sidewall through the bottom to the second sidewall;
the recess comprises two depressed outer arched sections that are spaced apart from each other by an inner section;
the outer arched sections are transverse to a longitudinal axis of the mold;
the inner section comprises a keel that extends upward from the bottom of the mold body;
a height of the keel and a depth of the notch set a size of a femoral component produced using the mold;
the keel is aligned with the notch when the piston is inserted within the femoral component mold; and
one or both of the notch and the keel comprise one or more calibration markings that indicate increments of adjustments to the size of the femoral component.

16. The femoral component kit of claim 15, wherein:
the piston further comprises a handle that is coupled with a top surface of the piston body.

17. The femoral component kit of claim 16, wherein:
the handle is spaced apart from the piston body.

18. The femoral component kit of claim 15, further comprising:
a preformed tibial component.

19. The femoral component kit of claim 18, wherein:
the preformed tibial component comprises polyethylene.

20. The femoral component kit of claim 15, further comprising:
a container of a bone cement powder; and
a container of a liquid monomer.

* * * * *